United States Patent
Kobayashi et al.

(10) Patent No.: US 11,046,655 B2
(45) Date of Patent: *Jun. 29, 2021

(54) COMPOUND AND METHOD FOR PRODUCING SAME

(71) Applicants: Sumitomo Chemical Company, Limited, Tokyo (JP); Cambridge Display Technology Limited, Cambridgeshire (GB)

(72) Inventors: Satoshi Kobayashi, Tsukuba (JP); Takayuki Iijima, Tsukuba (JP); Nobuhiko Akino, Tsukuba (JP); Sheena Zuberi, Godmanchester (GB)

(73) Assignees: SUMITOMO CHEMICAL COMPANY, LIMITED, Tokyo (JP); CAMBRIDGE DISPLAY TECHNOLOGY LIMITED, Cambridgeshire (GB)

(*) Notice: Subject to any disclaimer, the term of this patent is extended or adjusted under 35 U.S.C. 154(b) by 161 days.

This patent is subject to a terminal disclaimer.

(21) Appl. No.: 16/089,485

(22) PCT Filed: Mar. 21, 2017

(86) PCT No.: PCT/JP2017/011172
§ 371 (c)(1),
(2) Date: Sep. 28, 2018

(87) PCT Pub. No.: WO2017/169971
PCT Pub. Date: Oct. 5, 2017

(65) Prior Publication Data
US 2020/0140394 A1    May 7, 2020

(30) Foreign Application Priority Data
Mar. 29, 2016 (JP) .............................. JP2016-066102

(51) Int. Cl.
C07D 235/18    (2006.01)
H01L 51/50    (2006.01)

(52) U.S. Cl.
CPC ........ C07D 235/18 (2013.01); H01L 51/5076 (2013.01)

(58) Field of Classification Search
CPC .................................................. C07D 235/18
See application file for complete search history.

(56) References Cited

U.S. PATENT DOCUMENTS

| | | | |
|---|---|---|---|
| 10,711,091 B2* | 7/2020 | Iijima | H01L 51/5076 |
| 2010/0187515 A1 | 7/2010 | Limmert et al. | |
| 2011/0108772 A1 | 5/2011 | Zeika et al. | |
| 2012/0256296 A1 | 10/2012 | Wei et al. | |
| 2014/0070178 A1 | 3/2014 | Lee et al. | |
| 2015/0141656 A1 | 5/2015 | Koch | |

FOREIGN PATENT DOCUMENTS

| | | |
|---|---|---|
| CN | 106316960 A | 1/2017 |
| JP | 2007-273978 A | 10/2007 |
| JP | 2007-314513 A | 12/2007 |
| JP | 2008110935 A | 5/2008 |
| JP | 2008-214613 A | 9/2008 |
| JP | 2009-530836 A | 8/2009 |
| JP | 2010-532555 A | 10/2010 |

(Continued)

OTHER PUBLICATIONS

Chemical Abstracts Registry No. 2068754-42-5, indexed in the Registry file on STN CAS Online Feb. 9, 2017. (Year: 2017).*
Chemical Abstracts Registry No. 2068754-43-6, indexed in the Registry file on STN CAS Online Feb. 9, 2017. (Year: 2017).*
Chemical Abstracts Registry No. 2068754-30-1, indexed in the Registry file on STN CAS Online Feb. 9, 2017. (Year: 2017).*
An English machine translation of CN 106316960 A, Duan et al., Jan. 2017. (Year: 2017).*
An English machine translation of JP 2008-110935 A, Doi et al., May 15, 2008. (Year: 2008).*
Douhal et al., "Proton transfer spectroscopy of 2-(2'-hydroxyphenyl)imidazole and 2-(2'-hydroxyphenyl) benzimidazole dyes," J. Photochem. Photobiol. A. Chem., vol. 78, pp. 127-138 (1994).

(Continued)

*Primary Examiner* — Laura L Stockton
(74) *Attorney, Agent, or Firm* — Panitch Schwarze Belisario & Nadel LLP

(57) ABSTRACT

A compound represented by the formula (1) is provided:

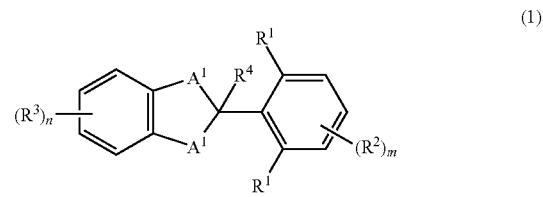

(1)

wherein $A^1$ represents an oxygen atom, a sulfur atom, $-NR^5-$ or $-PR^5-$; at least one $A^1$ is $-NR^5-$ or $-PR^5-$; $R^1$ represents a hydrogen atom, an alkyl group, a cycloalkyl group, an alkoxy group, a cycloalkoxy group, an aryloxy group, an alkylsulfenyl group, a cycloalkylsulfenyl group, an arylsulfenyl group or a disubstituted amino group; $R^2$ and $R^3$ represent an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; $R^4$ represents a hydrogen atom, $-C(R^6)_3$, $-OR^7$, $-N(R^7)_2$ or $-Si(R^7)_3$; m represents an integer of 0 to 3; and n represents an integer of 0 to 4.

9 Claims, No Drawings

(56) References Cited

FOREIGN PATENT DOCUMENTS

| JP | 2015-521173 A | 7/2015 |
| KR | 10-2016-0015644 A | 2/2016 |
| WO | 2011/127075 A1 | 10/2011 |

OTHER PUBLICATIONS

Office Action dated Oct. 15, 2019 in JP Application No. 2016066102.

Int'l Preliminary Report on Patentability dated Oct. 11, 2018 in Int'l Application No. PCT/JP2017/011172.

Int'l Search Report dated Jun. 6, 2017 in Int'l Application No. PCT/JP2017/011172.

Brunet et al, "Formal transfers of hydride from carbon-hydrogen bonds. Attempted generation of H2 by intramolecular protonolyses of the activated carbon-hydrogen bonds of dihydrobenzimidazoles," Canadian Journal of Chemistry, vol. 74, No. 5, pp. 689-696 (1996).

Wei et al, "Use of a 1H-Benzoimidazole Derivative as an n-Type Dopant and to Enable Air-Stable Solution-Processed n-Channel Organic Thin-Film Transistors," Journal of the AmericanChemical Society, vol. 132, No. 26, pp. 8852-8853 (2010).

Zhu et al, "Hydride, Hydrogen Atom, Proton, and Electron Transfer Driving Forces of Various Five-Membered Heterocyclic Organic Hydrides and Their Reaction Intermediates in Acetonitrile," Journal of the American Chemical Society, vol. 130, No. 8, pp. 2501-2516 (2008).

Rodriguez et al, "Oxaphosphole-Based Monophosphorus Ligands for Palladium-Catalyzed Amination Reactions," Advanced Synthesis & Catalysis, vol. 353, No. 4, pp. 533-537 (2011).

Tang et al, "Synthesis of o-[N-(Substituted benzoyl)-Nmethylamino]phenyl Disulfides by the Spontaneous Coupling of N-Methyl-2-mono(substituted phenyl) benzothiazolines in Solution and their VEGF Inhibitory Activities," Chinese Journal of Chemistry, vol. 26, No. 8, pp. 1447-1453 (2008).

Beveridge et al, "Copper-Catalyzed Multicomponent Coupling of Organoindium Reagents with Nitrogen-Containing Aromatic Heterocycles," European Journal of Organic Chemistry, vol. 19, pp. 3650-3656 (2010).

Office Action dated Jan. 12, 2021 in JP Application No. 2016066102.

\* cited by examiner

COMPOUND AND METHOD FOR PRODUCING SAME

CROSS-REFERENCE TO RELATED APPLICATION

This application is a Section 371 of International Application No. PCT/JP2017/011172, filed Mar. 21, 2017, which was published in the Japanese language on Oct. 5, 2017 under International Publication No. WO 2017/169971 A1, and claims priority under 35 U.S.C. § 119(b) to Japanese Application No. 2016-066102, filed Mar. 29, 2016.

TECHNICAL FIELD

The present invention relates to a novel compound and a method for producing the same.

BACKGROUND ART

In recent years, research on various electronic devices such as organic light-emitting diodes (OLED), polymer light-emitting diodes (PLED), organic photovoltaics (OPV), and organic thin film transistors (OTFT) using ultrathin films of organic materials has been actively made. For these electronic devices, methods using doping materials are known as methods for improving conductivity.

For example, an organic thin film transistor using N-DMBI as an n-type doping material is disclosed in Non Patent Literature 1; an organic light-emitting diode using N-DMBI as an n-type doping material is disclosed in Patent Literature 1; and an n-type dopant precursor for doping an organic semiconductor material is disclosed in Patent Literature 2.

CITATION LIST

Patent Literature

Patent Literature 1: U.S. Patent Application Publication No. 2010/0070178
Patent Literature 2: Japanese Unexamined Patent Publication No. 2010-532555

Non Patent Literature

Non Patent Literature 1: Bao et al., "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852

SUMMARY OF INVENTION

Technical Problem

However, sufficient findings on stable n-type doping materials that permit film formation by a coating method have not yet been obtained. For example, compounds described as n-type doping materials in the cited literatures mentioned above did not always have sufficient electron-donating ability.

Accordingly, an object of the present invention is to provide a novel compound that can be suitably used as a strong n-type doping material, and a method for producing the same.

Solution to Problem

The present invention provides the following [1] to [9]:
[1] A compound represented by the formula (1):

[Chemical Formula 1]

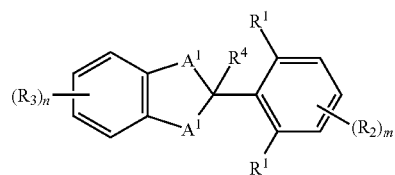

(1)

wherein
$A^1$ represents an oxygen atom, a sulfur atom, —$NR^5$— or —$PR^5$—; two $A^1$ are the same as or different from each other, and at least one $A^1$ is —$NR^5$— or —$PR^5$—;
$R^1$ represents a hydrogen atom, an alkyl group, a cycloalkyl group, an alkoxy group, a cycloalkoxy group, an aryloxy group, an alkylsulfenyl group, a cycloalkylsulfenyl group, an arylsulfenyl group or a disubstituted amino group; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time; two $R^1$ are the same as or different from each other;
$R^2$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time; in the case where m is 2 or larger, the plurality of $R^2$ are the same as or different from each other; adjacent $R^2$ are optionally bonded to each other to form a ring;
$R^3$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time; in the case where n is 2 or larger, the plurality of $R^3$ are the same as or different from each other; adjacent $R^3$ are optionally bonded to each other to form a ring,
provided that
in the case where n is 0 or in the case where $R^3$ is not a disubstituted amino group, at least one $R^1$ is an alkoxy group, a cycloalkoxy group, an aryloxy group, an alkylsulfenyl group, a cycloalkylsulfenyl group, an arylsulfenyl group or a disubstituted amino group, and
in the case where any of $R^1$, $R^2$ and $R^3$ are not a disubstituted amino group, both of two $R^1$ are groups other than a hydrogen atom, and at least one $R^1$ is an alkoxy group, a cycloalkoxy group, an aryloxy group, an alkylsulfenyl group, a cycloalkylsulfenyl group or an arylsulfenyl group;
$R^4$ represents a hydrogen atom, —C($R^6$)$_3$, —$OR^7$, —N($R^7$)$_2$ or —Si($R^7$)$_3$; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time;

$R^5$ represents an alkyl group, a cycloalkyl group, an aryl group or a monovalent heterocyclic group; —$CH_2$— in these groups is optionally replaced with an oxygen atom, a sulfur atom, —$NR^8$— or —C(=O)O—, and a portion or the whole of hydrogen atoms in these groups is optionally substituted with a halogen atom, provided that adjacent two —$CH_2$— are not replaced at the same time; When a plurality of $R^5$ are present, the plurality of $R^5$ are the same as or different from each other;

$R^6$ represents a hydrogen atom, an alkyl group, a cycloalkyl group, an aryl group or a monovalent heterocyclic group; a portion or the whole of hydrogen atoms in these groups is optionally substituted with a halogen atom; the plurality of $R^6$ are the same as or different from each other; two $R^6$ are optionally bonded to form a ring;

$R^7$ represents an alkyl group, a cycloalkyl group, an aryl group or a monovalent heterocyclic group; a portion or the whole of hydrogen atoms in these groups is optionally substituted with a halogen atom; a plurality of $R^7$ are the same as or different from each other; two $R^7$ are optionally bonded to faun a ring;

$R^8$ represents an alkyl group, a cycloalkyl group, an aryl group or a monovalent heterocyclic group; a portion or the whole of hydrogen atoms in these groups is optionally substituted with a halogen atom; when a plurality of $R^8$ are present, the plurality of $R^8$ are the same as or different from each other;

m represents an integer of 0 to 3; and n represents an integer of 0 to 4.

[2] The compound according to [1], wherein both of two $A^1$ are —$NR^5$—.

[3] The compound according to [1] or [2], wherein the compound is a compound represented by the formula (2):

[Chemical Formula 2]

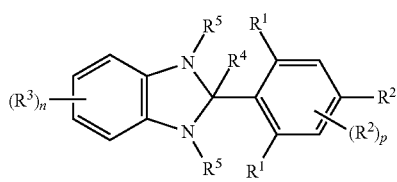

(2)

wherein $R^1$, $R^2$, $R^3$, $R^4$, $R^5$ and n are the same as above, and p represents an integer of 0 to 2.

[4] The compound according to any of [1] to [3], wherein $R^4$ is a hydrogen atom.

[5] A composition comprising the compound according to any of [1] to [4] and an electron-transporting material.

[6] A composition comprising the compound according to any of [1] to [4], an electron-transporting material and a solvent.

[7] A method for producing the compound according to any of [1] to [4], comprising a step of reacting a compound represented by the formula (3) with a compound represented by the formula (4):

[Chemical Formula 3]

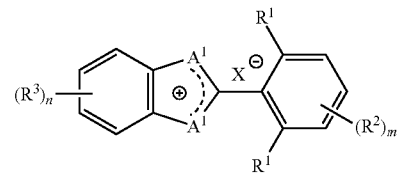

(3)

wherein $A^1$, $R^1$, $R^2$, $R^3$, m and n are the same as above, and $X^-$ represents a counter anion for the cation, and

[Chemical Formula 4]

$M^1{}_q(M^2\text{-}R^4{}_r)_s$ (4)

wherein $R^4$ is the same as above, $M^1$ and $M^2$ each independently represent a group containing a metal atom or a metalloid atom, q represents an integer of 0 to 3, r represents an integer of 1 to 4, and s represents an integer of 1 to 3.

[8] The method according to [7], wherein $R^4$ is a hydrogen atom, and $M^2$ is an aluminum atom.

[9] A compound represented by the formula (3).

Advantageous Effects of Invention

The compound according to the present invention is relatively stable in a solvent, can be applied to film formation by a coating method, and suitably functions as an n-type doping material. Also, the compound according to the present invention can dope a electron-transporting material more strongly by mixing the compound with the electron-transporting material, as compared with a publicly known n-type doping material that permits film formation by a coating method.

DESCRIPTION OF EMBODIMENTS

Hereinafter, preferable embodiments of the present invention will be described in detail.

Description of Common Terms

The terms commonly used in the present specification have the following meanings unless otherwise specified.

Me represents a methyl group, Et represents an ethyl group, Bu represents a butyl group, i-Pr represents an isopropyl group, t-Bu represents a tert-butyl group, and Ph represents a phenyl group.

The hydrogen atom may be a heavy hydrogen atom or may be a light hydrogen atom.

The "alkyl group" may be linear or branched. The number of carbon atoms of the linear alkyl group is usually 1 to 50, preferably 1 to 10, which excludes the number of carbon atoms of a substituent. The number of carbon atoms of the branched alkyl group is usually 3 to 50, preferably 3 to 10, which excludes the number of carbon atoms of a substituent.

The alkyl group optionally has a substituent. Examples of the alkyl group include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyl-decyl group, a dodecyl group or the like. Alternatively, the alkyl group optionally has a substituent and can be, for example, a group in which a portion or the whole of hydrogen atoms in these groups is substituted with a cycloalkyl group, an alkoxy group, a cycloalkoxy group, an aryl group, a fluorine atom or the like. Examples of such an alkyl group include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl)propyl group and a 6-ethyloxyhexyl group.

The number of carbon atoms of the "cycloalkyl group" is usually 3 to 50, preferably 3 to 10, which excludes the number of carbon atoms of a substituent.

The cycloalkyl group optionally has a substituent. Examples of the cycloalkyl group include a cyclohexyl group, a cyclohexylmethyl group and a cyclohexylethyl group.

The "aryl group" means a remaining atomic group excluding from an aromatic hydrocarbon one hydrogen atom directly bonded to an annular carbon atom. The number of carbon atoms of the aryl group is usually 6 to 60, preferably 6 to 20, which excludes the number of carbon atoms of a substituent.

The aryl group optionally has a substituent. Examples of the aryl group include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group or the like. Alternatively, the aryl group optionally has a substituent and can be, for example, a group in which a portion or the whole of hydrogen atoms in these groups is substituted with an alkyl group, a cycloalkyl group, an alkoxy group, a cycloalkoxy group, an aryl group, a fluorine atom or the like.

The "alkoxy group" may be linear or branched. The number of carbon atoms of the linear alkoxy group is usually 1 to 50, preferably 1 to 10, which excludes the number of carbon atoms of a substituent. The number of carbon atoms of the branched alkoxy group is usually 3 to 50, preferably 3 to 10, which excludes the number of carbon atoms of a substituent.

The alkoxy group optionally has a substituent. Examples of the alkoxy group include a methoxy group, an ethoxy group, a propyloxy group, an isopropyloxy group, a butyloxy group, an isobutyloxy group, a test-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group, a lauryloXy group or the like. Alternatively, the alkoxy group optionally has a substituent and can be, for example, a group in which a portion or the whole of hydrogen atoms in these groups is substituted with a cycloalkyl group, an alkoxy group, a cycloalkoxy group, an aryl group, a fluorine atom or the like.

The number of carbon atoms of the "cycloalkoxy group" is usually 3 to 50, preferably 3 to 10, which excludes the number of carbon atoms of a substituent.

The cycloalkoxy group optionally has a substituent. Examples of the cycloalkoxy group include a cyclohexyloxy group.

The number of carbon atoms of the aryloxy group is usually 6 to 60, preferably 6 to 20, which excludes the number of carbon atoms of a substituent.

The aryloxy group optionally has a substituent. Examples of the aryloxy group include a phenoxy group, a 1-naphthyloxy group, a 2-naphthyloxy group, a 1-anthracenyloxy group, a 9-anthracenyloxy group, a 1-pyrenyloxy group or the like. Alternatively, the aryloxy group optionally has a substituent and can be, for example, a group in which a portion or the whole of hydrogen atoms in these groups is substituted with an alkyl group, a cycloalkyl group, an alkoxy group, a cycloalkoxy group, a fluorine atom or the like.

The "alkylsulfenyl group" may be linear or branched. The number of carbon atoms of the linear alkylsulfenyl group is usually 1 to 50, preferably 1 to 10, which excludes the number of carbon atoms of a substituent. The number of carbon atoms of the branched alkylsulfenyl group is usually 3 to 50, preferably 3 to 10, which excludes the number of carbon atoms of a substituent.

The alkylsulfenyl group optionally has a substituent. Examples of the alkylsulfenyl group include a methylsulfenyl group, an ethylsulfenyl group, a propylsulfenyl group, an isopropylsulfenyl group, a butylsulfenyl group, an isobutylsulfenyl group, a tert-butylsulfenyl group, a pentylsulfenyl group, a hexylsulfenyl group, a heptylsulfenyl group, an octylsulfenyl group, a 2-ethylhexylsulfenyl group, a nonylsulfenyl group, a decylsulfenyl group, a 3,7-dimethyloctylsulfenyl group, and a laurylsulfenyl group. Alternatively, the alkylsulfenyl group may be a group in which a portion or the whole of hydrogen atoms in these groups is substituted with a cycloalkyl group, an alkoxy group, a cycloalkoxy group, an aryl group, a fluorine atom or the like.

The number of carbon atoms of the "cycloalkylsulfenyl group" is usually 3 to 50, preferably 3 to 10, which excludes the number of carbon atoms of a substituent.

The cycloalkylsulfenyl group optionally has a substituent. Examples of the cycloalkylsulfenyl group include a cyclohexylsulfenyl group.

The number of carbon atoms of the "arylsulfenyl group" is usually 6 to 60, preferably 6 to 20, which excludes the number of carbon atoms of a substituent.

The arylsulfenyl group optionally has a substituent. Examples of the arylsulfenyl group include a phenylsulfenyl group, a 1-naphthylsulfenyi group, a 2-naphthylsulfenyl group, a 1-anthracenylsulfenyl group, a 9-anthracenylsulfenyl group, and a 1-pyrenylsulfenyl group. Alternatively, the arylsulfenyl group may be a group in which a portion or the whole of hydrogen atoms in these groups is substituted with an alkyl group, a cycloalkyl group, an alkoxy group, a cycloalkoxy group, a fluorine atom or the like.

The "monovalent heterocyclic group" means a remaining atomic group excluding from a heterocyclic compound a hydrogen atom among hydrogen atoms directly bonded to annular carbon atoms or heteroatoms. Among the monovalent heterocyclic groups, a "monovalent aromatic heterocyclic group" is preferable Which is a remaining atomic group excluding from an aromatic heterocyclic compound a hydrogen atom among hydrogen atoms directly bonded to annular carbon atoms or heteroatoms.

The "aromatic heterocyclic compound" means a compound in which a heterocyclic ring itself exhibits aromaticity, such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, or dibenzophosphole, and a compound in which an aromatic ring is condensed with a heterocyclic ring even though the heterocyclic ring itself does not aromaticity, such as phenoxazine, phenothiazine, dibenzoborole, dibenzosilole, or benzopyran.

The number of carbon atoms of the monovalent heterocyclic group is usually 2 to 60, preferably 2 to 20, which excludes the number of carbon atoms of a substituent.

The monovalent heterocyclic group optionally has a substituent. Examples of the monovalent heterocyclic group include a thienyl group, a pyrrolyl group, a furyl group, a pyridyl group, a piperidinyl group, a quinolinyl group, an isoquinolinyl group, a pyrimidinyl group, a triazinyl group or the like. Alternatively, the monovalent heterocyclic group optionally has a substituent and can be, for example, a group in which a portion or the whole of hydrogen atoms in these groups is substituted with an alkyl group, a cycloalkyl group, an alkoxy group, a cycloalkoxy group or the like.

The "halogen atom" refers to a fluorine atom, a chlorine atom, a bromine atom or an iodine atom.

The "amino group" optionally has a substituent, and a substituted amino group is preferable. An alkyl group, a cycloalkyl group, an aryl group or a monovalent heterocyclic group is preferable as the substituent carried by the amino group.

A disubstituted amino group is preferable as the substituted amino group. A combination from an alkyl group, a cycloalkyl group, and an aryl group is preferable as the substituents of the disubstituted amino group. A dialkylamino group or a dicycloalkylamino group is preferable as the disubstituted amino group, and a dialkylamino group is more preferable.

Examples of the disubstituted amino group include a dialkylamino group, a dicycloalkylamino group and a diarylamino group. The substituents of the disubstituted amino group are optionally bonded to each other to form a ring. The number of carbon atoms of the alkyl group as the substituent of the disubstituted amino group is usually 1 to 50, preferably 1 to 1.0.

Examples of the disubstituted amino group include a dimethylamino group, a diethylamino group, a diphenylamino group, a bis(4-methylphenyl)amino group, a bis(4-tert-butylphenyl)amino group, a bis(3,5-di-tort-butylphenyl)amino group, a pyrrolidinyl group, a piperidinyl group, and a carbazolyl group.

The "substituent" represents a halogen atom, a cyano group, an alkyl group, a cycloalkyl group, an aryl group, a monovalent heterocyclic group, an alkoxy group, a cycloalkoxy group, an aryloxy group or an amino group.

The compound according to the present embodiment is a compound represented by the formula (1):

[Chemical Formula 5]

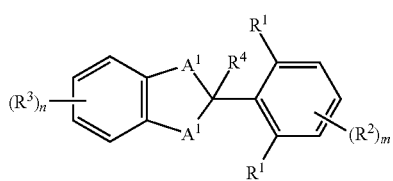

(1)

It is preferable for $A^1$ that both of two $A^{1'}$ should be —$NR^5$— or —$PR^5$—. Such a compound is represented by, for example, the formula (1-2):

[Chemical Formula 6]

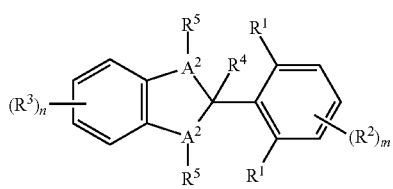

(1-2)

In the formula, $R^1$, $R^2$, $R^3$, $R^4$, $R^5$, n and m are the same as above, and $A^2$ represents a nitrogen atom or a phosphorus atom. Two $A^2$ are the same as or different from each other.

It is more preferable for $A^1$ that both of two $A^1$ should be —$NR^5$—.

It is preferable that $R^1$ should be a group having strong electron-donating ability, because the compound according to the present embodiment functions as a stronger dopant. It is preferable that at least one $R^1$ should be an alkoxy group, a cycloalkoxy group, an aryloxy group or a disubstituted amino group, and it is more preferable that at least one $R^1$ should be an alkoxy group.

Provided that two $R^1$ are alkoxy groups, cycloalkoxy groups, aryloxy groups, alkylsulfenyl groups, cycloalkylsulfenyl groups, arylsulfenyl groups or disubstituted amino groups, the compound according to the present embodiment is capable of sufficiently functioning as a strong dopant even in the case where $R^2$ and $R^3$ are any of those mentioned above. Specifically, in a preferable aspect, both of two $R^1$ can be alkoxy groups, cycloalkoxy groups, aryloxy groups, alkylsulfenyl groups, cycloalkylsulfenyl groups, arylsulfenyl groups or disubstituted amino groups. In this aspect, it is preferable that both of two $R^1$ should be alkoxy groups, cycloalkoxy groups, aryloxy groups or disubstituted amino groups, and it is more preferable to be an alkoxy group.

It is preferable that $R^2$ should be a group having strong electron-donating ability, because the compound according to the present embodiment functions as a stronger dopant. It is preferable that $R^2$ should be an alkoxy group, a cycloalkoxy group, an aryloxy group, an alkylsulfenyl group, a cycloalkylsulfenyl group, an arylsulfenyl group or a disubstituted amino group, it is more preferable to be an alkoxy group or a disubstituted amino group, and it is further preferable to be a disubstituted amino group.

It is preferable that $R^3$ should be a group having strong electron-donating ability, because the compound according to the present embodiment functions as a stronger dopant. It is preferable that $R^3$ should be an alkoxy group, a cycloalkoxy group, an aryloxy group, an alkylsulfenyl group, a cycloalkylsulfenyl group, an arylsulfenyl group or a disubstituted amino group, and it is more preferable to be a disubstituted amino group.

Provided that n is 1 or larger and at least one $R^3$ is a disubstituted amino group, the compound according to the present embodiment is capable of sufficiently functioning as a strong dopant even in the case where $R^1$ and $R^2$ are any of those mentioned above. Specifically, in the compound according to a preferable aspect, n can be 1 or large, and at least one $R^3$ can be a disubstituted amino group.

It is preferable that $R^4$ should be a hydrogen atom, an alkyl group or an aryl group, and it is more preferable to be a hydrogen atom, because synthesis is easy.

It is preferable that $R^5$ should be an alkyl group or a cycloalkyl group, and it is more preferable to be an alkyl group.

It is preferable that an electron-donating group should be bonded to the para position of the benzene ring bonded to the benzimidazoline ring, because the compound according to the present embodiment functions as a stronger dopant. Such a compound is represented by, for example, the formula (2):

[Chemical Formula 7]

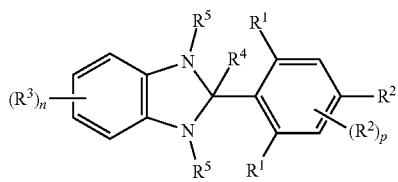

(2)

In the formula (2), it is preferable that R² bonded to the para position of the benzene ring (hereinafter, also referred to as R² of the para position) should be an alkoxy group, a cycloalkoxy group, an aryloxy group, an alkylsulfenyl group, a cycloalkylsulfenyl group, an arylsulfenyl group or a disubstituted amino group, it is more preferable to be an alkoxy group or a disubstituted amino group, and it is further preferable to be a disubstituted amino group.

In the formula (2), when R² of the para position is a disubstituted amino group, it is preferable that R¹ should be a hydrogen atom, an alkoxy group, a cycloalkoxy group, an aryloxy group, an alkylsulfenyl group, a cycloalkylsulfenyl group, an arylsulfenyl group or a disubstituted amino group. Although two R¹ are the same as or different from each other, at least one R¹ is a group other than a hydrogen atom. In this respect, it is more preferable that the group other than a hydrogen atom in R¹ should be an alkoxy group, a cycloalkoxy group, an aryloxy group or a disubstituted amino group, and it is further preferable to be an alkoxy group.

In the formula (2), when R² of the para position is a group other than a disubstituted amino group, it is preferable that R¹ should be an alkoxy group, a cycloalkoxy group, an aryloxy group, an alkylsulfenyl group, a cycloalkylsulfenyl group, an arylsulfenyl group or a disubstituted amino group, it is more preferable to be an alkoxy group, a cycloalkoxy group, an aryloxy group or a disubstituted amino group, and it is further preferable to be an alkoxy group or a disubstituted amino group. In this respect, it is preferable for R² of the para position that the group other than a disubstituted amino group should be an alkoxy group, a cycloalkoxy group, an aryloxy group, an alkylsulfenyl group, a cycloalkylsulfenyl group or an arylsulfenyl group, and it is more preferable to be an alkoxy group.

In the formula (2), p can be 0. In the formula (2), n can be 0 to 2, can be 0 or 1, and can be 0.

Among the compounds represented by the formula (1), a compound is preferable in which at least one R¹ is an alkoxy group, a cycloalkoxy group, an aryloxy group, an alkylsulfenyl group, a cycloalkylsulfenyl group, an arylsulfenyl group or a disubstituted amino group, and in the case where any of R¹ and R² are not a disubstituted amino group, both of two R¹ are groups other than a hydrogen atom, and at least one R¹ is an alkoxy group, a cycloalkoxy group, an aryloxy group, an alkylsulfenyl group, a cycloalkylsulfenyl group or an arylsulfenyl group.

It is preferable that an electron-donating group should be bonded to R² of the para position, because the compound according to the present embodiment functions as a stronger dopant. Such a compound is, for example, a compound represented by the formula (2) which is a compound in which at least one R¹ is an alkoxy group, a cycloalkoxy group, an aryloxy group, an alkylsulfenyl group, a cycloalkylsulfenyl group, an arylsulfenyl group or a disubstituted amino group, and in the case where any of R¹ and R² of the para position are not a disubstituted amino group, both of two R¹ are groups other than a hydrogen atom, and at least one R¹ is an alkoxy group, a cycloalkoxy group, an aryloxy group, an alkylsulfenyl group, a cycloalkylsulfenyl group or an arylsulfenyl group.

In this context, it is preferable that R² of the para position should be an alkoxy group, a cycloalkoxy group, an aryloxy group, an alkylsulfenyl group, a cycloalkylsulfenyl group, an arylsulfenyl group or a disubstituted amino group, and it is more preferable to be a disubstituted amino group.

Examples of the compound according to the present embodiment include compounds represented by the following formulas:

[Chemical Formula 8]

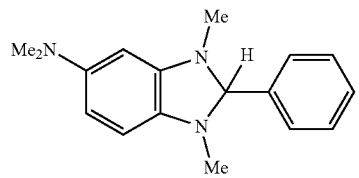

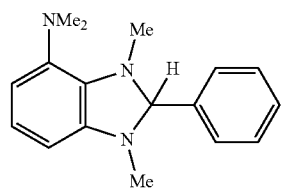

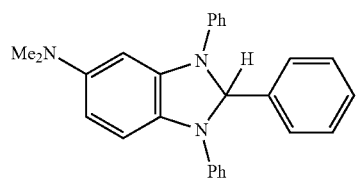

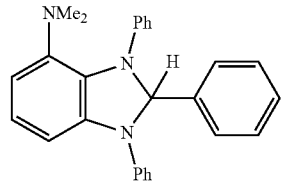

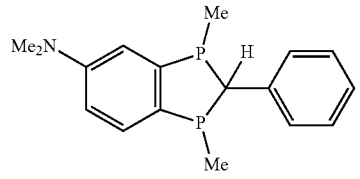

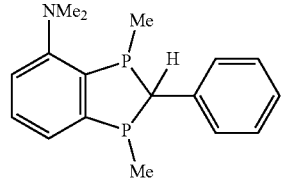

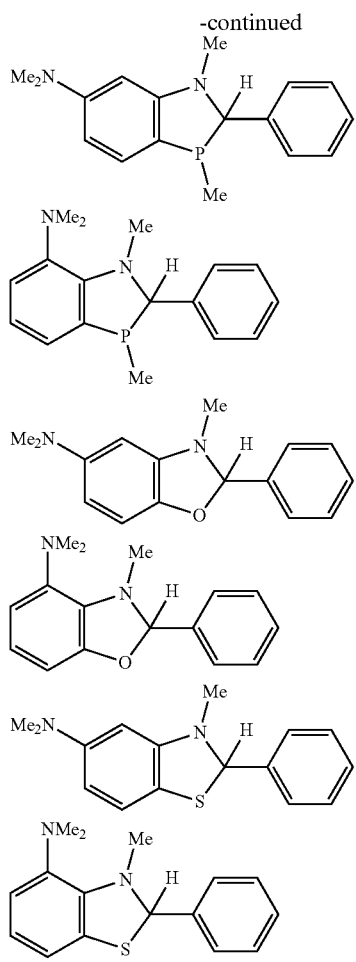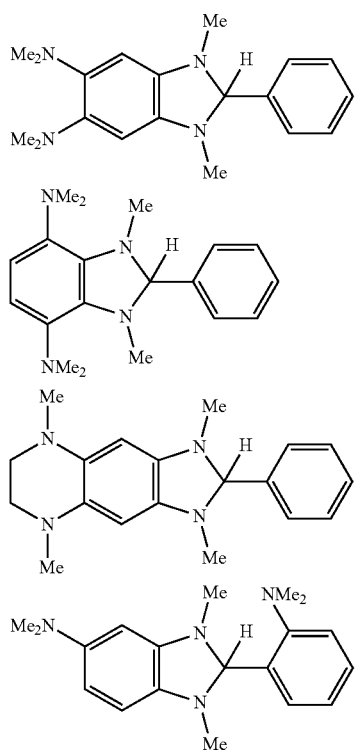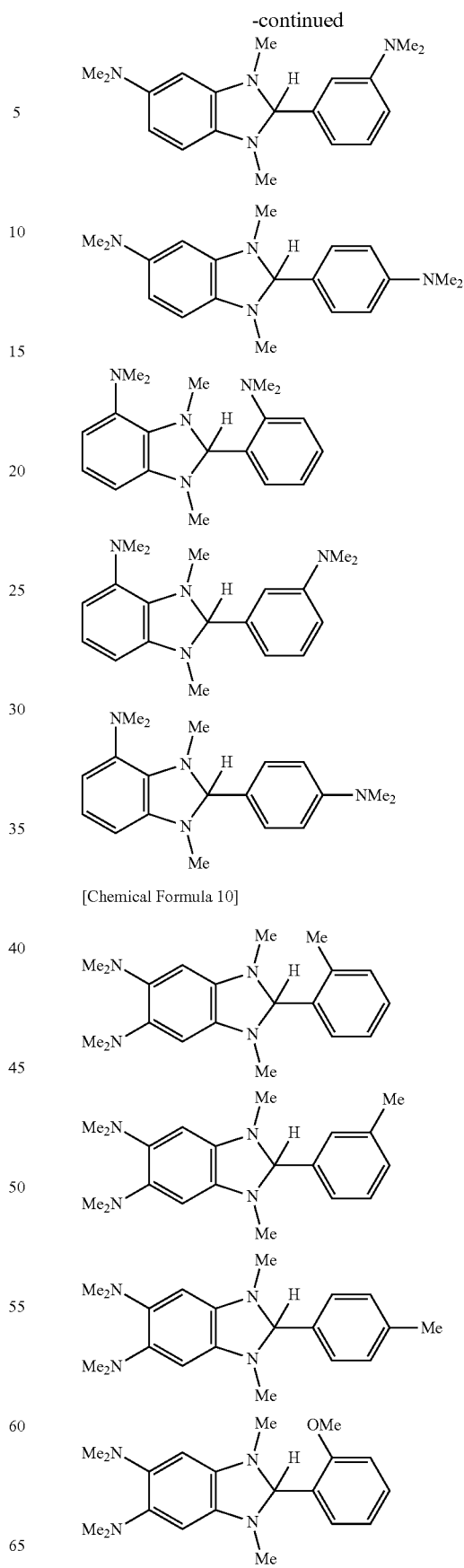

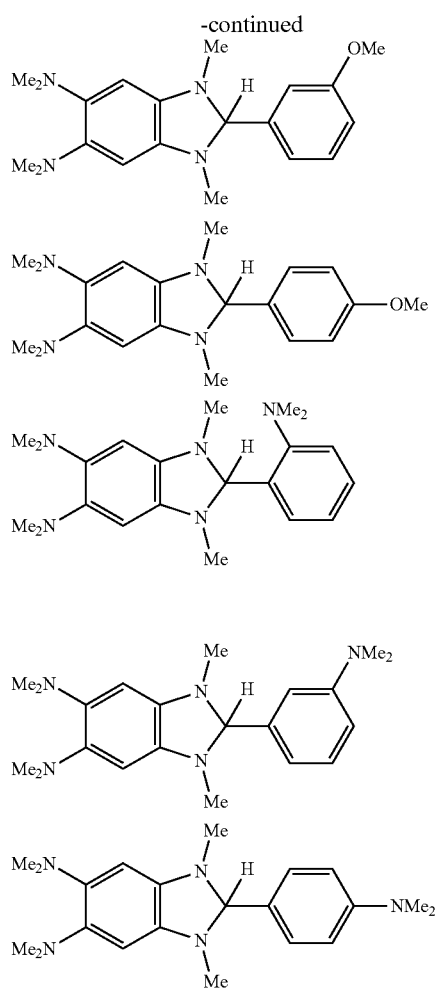
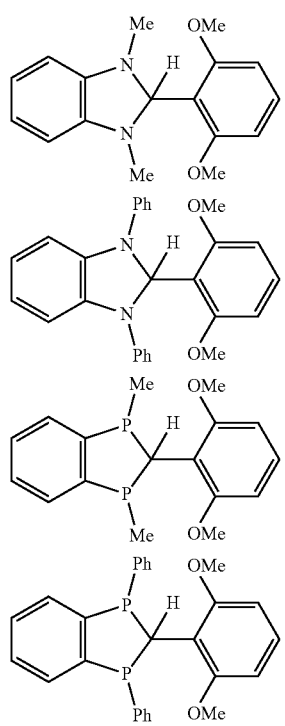
[Chemical Formula 11]
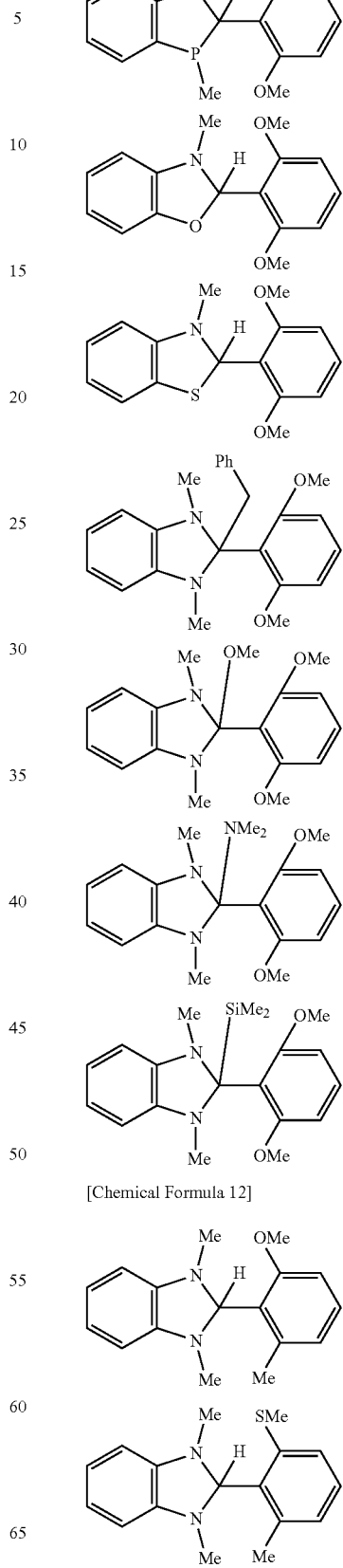
[Chemical Formula 12]

-continued
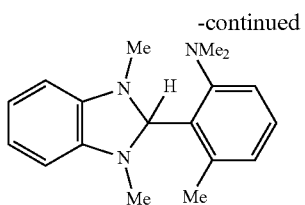
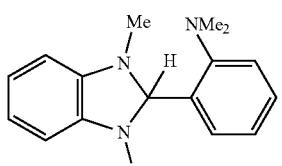
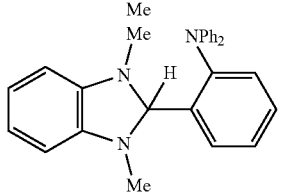
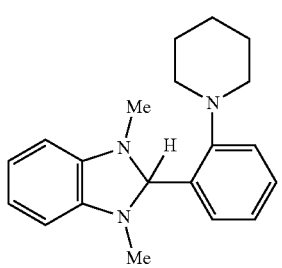
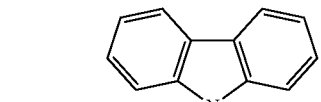
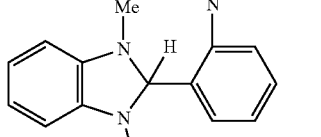
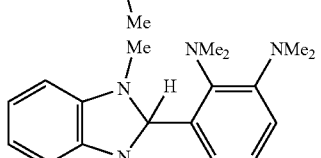
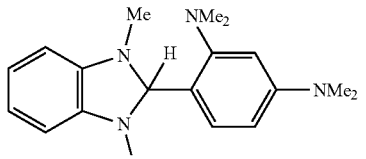
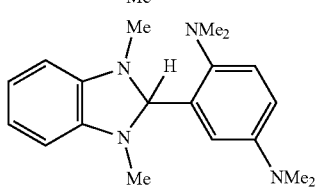
-continued
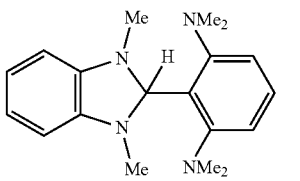
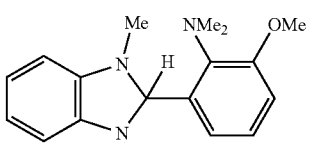
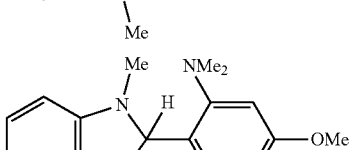
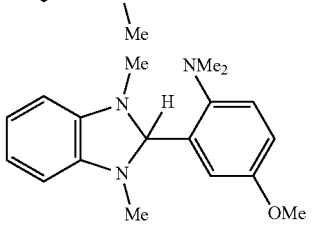
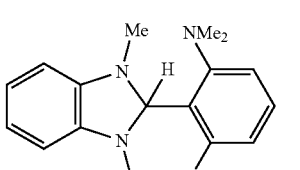
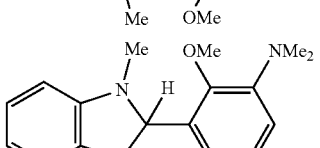
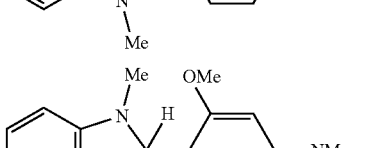
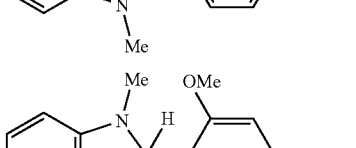
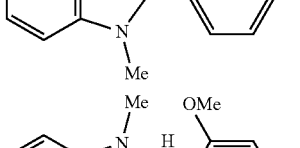
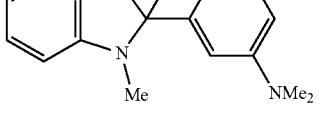

[Chemical Formula 13]
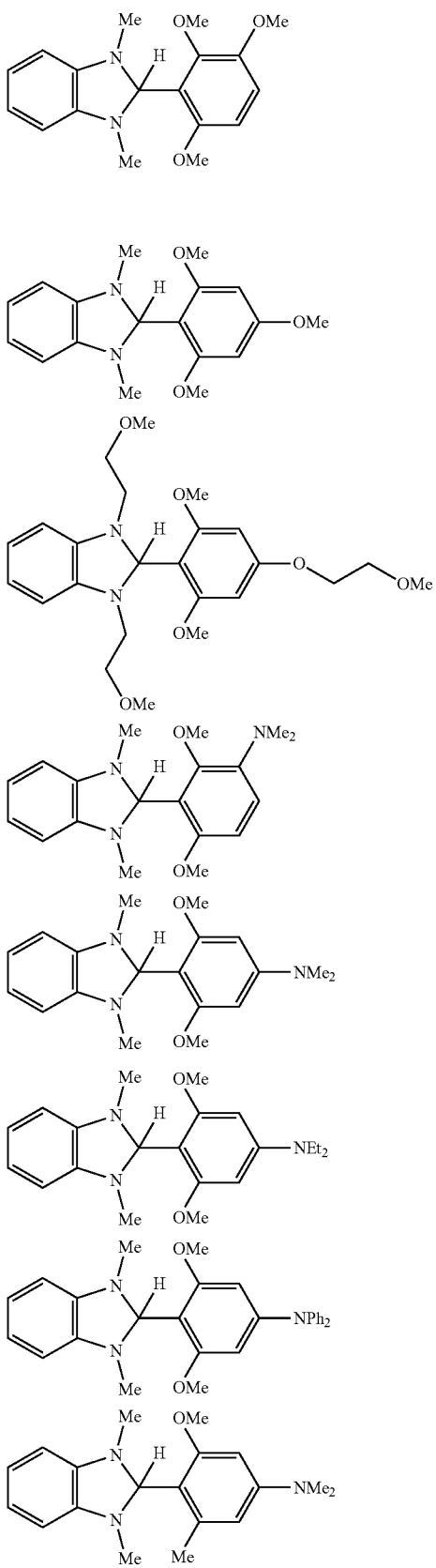
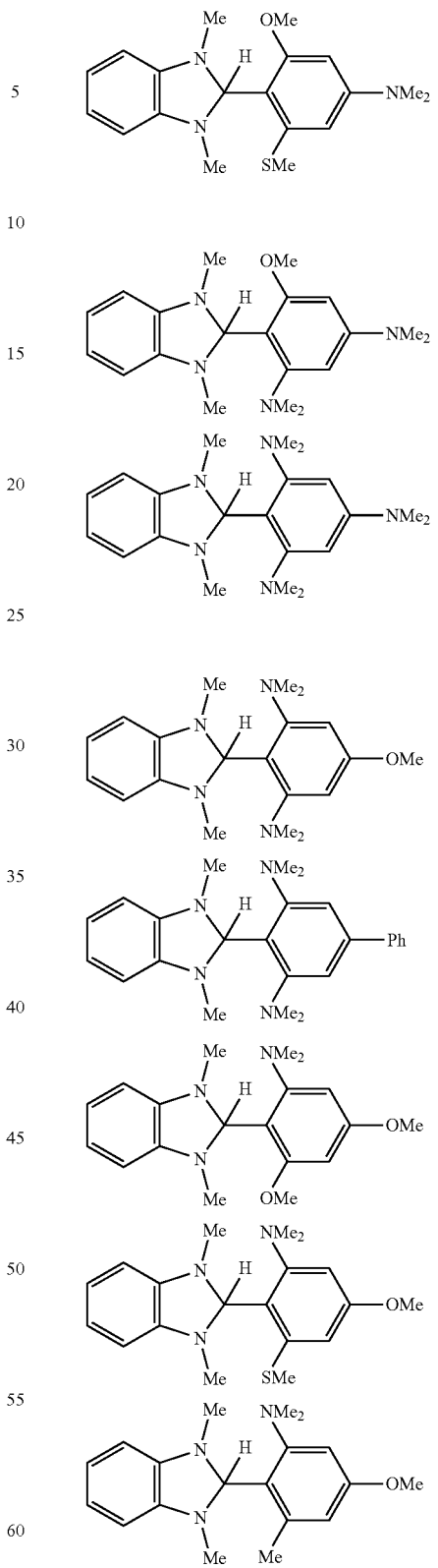
The compound according to the present embodiment can be produced, for example, by reacting a compound represented by the formula (3) with a compound represented by the formula (4),

[Chemical Formula 14]

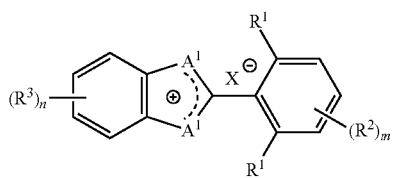

(3)

[Chemical Formula 15]

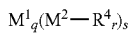

(4)

Examples of the counter anion represented by $X^-$ include hydroxide ions, halide ions, carboxylate ions, carbonate ions, sulfate ions, nitrate ions, phosphate ions, and nitrate ions, and hydroxide ions and halide ions are preferable.

The metal atom or the metalloid atom contained in $M^1$ can be, for example, an alkali metal atom, an alkaline earth metal atom, a transition metal atom, a zinc group atom or a boron group atom. It is preferable that $M^1$ should be a group containing an alkali metal atom or an alkaline earth metal atom, and it is more preferable to be a group containing an alkali metal atom. Preferable examples of the metal atom or the metalloid atom contained in $M^1$ include a lithium atom, a sodium atom, a potassium atom, a magnesium atom, and a calcium atom.

The metal atom or the metalloid atom contained in $M^2$ can be, for example, an alkali metal atom, an alkaline earth metal atom, a transition metal atom, a zinc group atom or a boron group atom. $M^2$ can be, for example, a group containing a lithium atom, a sodium atom, a potassium atom, a magnesium atom, a calcium atom, an iron atom, a cobalt atom, a nickel atom, a copper atom, a zinc atom, a boron atom or an aluminum atom.

Examples of the compound represented by the formula (4) include hydride reducing agents such as sodium borohydride, lithium aluminum hydride, and diisopropyl aluminum hydride, organolithium reagents, Grignard reagents, organozinc reagents, organoaluminum reagents, ate complexes, metal alkoxides and metal amides.

Among the compounds represented by the formula (1), in the case of producing a compound in which $R^4$ is a hydrogen atom, it is preferable to use a compound in which $M^2$ is aluminum (Al) as the compound represented by the formula (4), and it is more preferable to use lithium aluminum hydride ($LiAlH_4$), because favorable yields are easily obtained.

As mentioned above, the compound represented by the formula (3) is useful as an intermediate for the synthesis of the compound represented by the formula (1). In this context, examples and preferable ranges of $A^1$, $R^1$, $R^2$, $R^3$, m and n in the formula (3) are the same as the examples and the preferable ranges of $A^1$, $R^1$, $R^2$, $R^3$, m and n in the formula (1). Specific examples of the compound represented by the formula (3) include precursors of the listed compounds as the compound represented by the formula (1).

The compound according to the present embodiment can be suitably used as an n-type doping material.

The compound according to the present embodiment is mixed with, for example, an electron-transporting material, and a thin film can be formed and activated by heat or light irradiation to thereby n-dope the electron-transporting material. Therefore, the thin film containing the compound according to the present embodiment and the electron-transporting material can be suitably used in various electronic devices such as organic EL, polymer light-emitting diodes, organic photovoltaics, and organic thin film transistors.

It is preferable that the electron-transporting material should be a compound whose LUMO level is −2.0 eV or less. The compound according to the present embodiment can n-dope an electron-transporting material of shallower LUMO, as compared with a publicly known N-DMBI-type compound. Therefore, the electron-transporting material can be a compound whose LUMO level is −3.0 eV or more and −2.0 eV or less.

The electron-transporting material can be classified into a low-molecular compound and a polymer compound.

Examples of the low-molecular compound include a metal complex with 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene and diphenoquinone, and their derivatives.

Examples of the polymer compound include polyphenylene, polyfluorene, polyphenylenevinylene, poly hienylenevinylene, polyquinoline and polyquinoxaline, and their derivatives.

It is preferable that the content of the compound according to the present embodiment with respect to 100 parts by mass of the electron-transporting material should be 0.1 to 200 parts by mass. The content is preferably 1 part by mass or more, more preferably 5 parts by mass or more, because the electron-transporting material can be more efficiently doped. Also, the content is preferably 50 parts by mass or less because film formability as an electron-transporting layer becomes favorable.

Examples of a method for forming the thin film include a vacuum deposition method from a powder and a method of forming a film from a solution or a melted state in the case of using a low-molecular compound as the electron-transporting material, and include a method of forming a film from a solution or a melted state in the case of using a polymer compound as the electron-transporting material.

The solvent that is used in the film formation method from a solution can be a solvent that can dissolve or uniformly disperse each material. Examples of the solvent include: chlorine-based solvents such as 1,2-dichloroethane, 1,1,2-trichloroethane, chlorobenzene, and o-dichlorobenzene; ether solvents such as THF, dioxane, anisole, and 4-methylanisole; aromatic hydrocarbon solvents such as toluene, xylene, mesitylene, ethylbenzene, pentylbenzene, hexylbenzene, heptylbenzene, octylbenzene, nonylbenzene, decylbenzene, undecylbenzene, dodecylbenzene, cyclohexylbenzene, trimethylbenzene, and 3-phenoxytoluene; aliphatic hydrocarbon solvents such as cyclohexane, methylcyclohexane, n-pentane, n-hexane, n-heptane, n-octane, n-nonane, n-decane, n-dodecane, and bicyclohexyl; ketone solvents such as acetone, methyl ethyl ketone, cyclohexanone, and acetophenone; ester solvents such as ethyl acetate, butyl acetate, ethylcellosolve acetate, methyl benzoate, and phenyl acetate; poly-hydric alcohol solvents such as ethylene glycol, glycerin, and 1,2-hexanediol; alcohol solvents such as methanol, ethanol, isopropyl alcohol, 1-butanol, tert-butyl alcohol, and cyclohexanol; sulfoxide solvents such as dimethyl sulfoxide; amide solvents such as N-methyl-2-pyrrolidone and N,N-dimethylformamide; fluorinated alcohol solvents such as 2,2,3,3-tetrafluoropropanol, 1,1,1-trifluoro-2-propanol, 1,1,1,3,3,3-hexafluoro-2-propanol, 2,2,3,3,4,4-hexafluorobutanol, 2,2,3,3,4,4,4-heptafluoro-1-butanol, 2,2,3,3,3-pentafluoro-1-propanol, 3,3,4, 4,5,5,5-heptafluoro-2-pentanol, 2,2,3,3,4,4,5,5-octafluoro-1-pentanol, 3,3,4,4,5,5,6,6,6-nonafluoro-1-hexanol, and 2,2,3,3,4,4,5,5,6,6,7,7-dodecafluoroheptanol; and water. One solvent may be used alone, or two or more may be used in combination.

It is preferable that the solvent should be a chlorine-based solvent, an ether solvent, an aromatic hydrocarbon solvent, a ketone solvent, an ester solvent or a combination thereof, because of being excellent in the stability and solubility of the compound according to the present embodiment.

Examples of the film formation method from a solution include coating methods such as a spin coating method, a casting method, a micro-gravure printing method, a gravure printing method, a bar coating method, a roll coating method, a wire bar coating method, a dip coating method, a slit coating method, a cap coating method, a spray coating method, a screen printing method, a flexographic printing method, an offset printing method, an inkjet printing method, and a nozzle coating method.

In the film formation method from a solution, the viscosity of the solution can be adjusted by the type of the film formation method. In the case of being applied to, for example, a printing method in which the solution passes through a discharge apparatus, such as an inkjet printing method, it is preferable that the viscosity of the solution should be 1 to 20 mPa·s at 25° C., because clogging or curved flight at the time of discharge is less likely to occur.

In the solution used in the film formation, the content of the solvent is usually 1000 to 100000 parts by mass, preferably 2000 to 20000 parts by mass, with respect to 100 parts by mass of the solute.

The activation of the thin film can be performed by heat or light irradiation. The timing of the activation treatment may be during the preparation of the thin film or may be after the thin film preparation. It is preferable that the activation treatment should be performed, after the thin film is sealed to create a state in which oxygen and water are blocked following the preparation of the thin film.

Examples of the activation method by heat include heating using an oven, heating using a hot plate, infrared heating, and heating by vacuum deposition energy.

Examples of the activation method by light irradiation include a method of performing irradiation with light using a light source that can emit any light of ultraviolet light, visible light and infrared light. It is preferable to use a light source that can emit any light of ultraviolet light and visible light, because the intensity of the light necessary for activation is easily obtained.

Although the preferable embodiments relating to the novel compound of the present invention are described above, the present invention is not limited by the embodiments described above.

One aspect of the present invention relates to a composition comprising the compound represented by the formula (1) and an electron-transporting material. The composition is prepared into a thin film form and can thereby be suitably used in various electronic devices such as organic EL, polymer light-emitting diodes, organic photovoltaics, and organic thin film transistors.

One aspect of the present invention also relates to a composition comprising the compound represented by the formula (1), an electron-transporting material and a solvent. By using the composition, a thin film suitable for application to various electronic devices can be easily prepared.

One aspect of the present invention also relates to a compound represented by the formula (3). According to the compound represented by the formula (3), the compound represented by the formula (1) can be easily synthesized.

One aspect of the present invention also relates to a method for producing the compound represented by the formula (1), comprising a step of reacting a compound represented by the formula (3) with a compound represented by the formula (4). According to this production method, the compound represented by the formula (1) can be easily synthesized.

EXAMPLES

Although the present invention will be described below more specifically with reference to Examples, the present invention is not limited by these Examples.

<Measurement of NMR>

The measurement of NMR was performed by the following method.

Approximately 10 mg of a measurement sample was dissolved in approximately 0.7 mL of a deuterated solvent and subjected to measurement using a NMR apparatus (manufactured by JEOL Ltd., product name: JNM-ECZ400S/L1).

<TLC-MS>

TLC-MS was measured by the following method.

A measurement sample was dissolved at an arbitrary concentration in toluene, tetrahydrofuran or chloroform, applied onto a TLC plate for DART (manufactured by Techno Applications Co., Ltd., trade name: YSK5-100) or a glass plate, and subjected to measurement using TLC-MS (manufactured by JEOL Ltd., trade name: JMS-T100TD (The AccuTOF TLC)). The helium gas temperature at the time of measurement was adjusted in the range of 200 to 400° C.

<Liquid Chromatography-Mass Spectrometry>

Liquid chromatography-mass spectrometry (LC-MS) was performed by the following method.

A measurement sample was dissolved in chloroform or THF so as to attain a concentration of approximately 2 mg/mL, and approximately 1 μL was injected to LC-MS (manufactured by Agilent Technologies, Inc., trade name: 1100LCMSD). Acetonitrile and THF were used at varying ratios as mobile phase of LC-MS, and the mobile phase was flowed at a flow rate of 0.2 mL/min. The column employed SUMIPAX ODS Z-CLUE 04.6×250 mm, 3 μm, manufactured by Sumika Chemical Analysis Service, Ltd.).

<Measurement of Number-Average Molecular Weight and Weight-Average Molecular Weight>

The polystyrene-based number-average molecular weight and the weight-average molecular weight of a polymer compound were determined by size exclusion chromatography (SEC) (manufactured by Shimadzu Corp., trade name: LC-10Avp).

The polymer compound to be measured was dissolved in tetrahydrofuran so as to attain a concentration of approximately 0.5% by weight, and 50 μL was injected to SEC. Tetrahydrofuran was used as a mobile phase of SEC and was flawed at a flow rate of 0.6 mL/min. Two TSKgel SuperHM-H (manufactured by Tosoh Corp.) and one TSKgel SuperH2000 (manufactured by Tosoh Corp.) were connected in series and used as a column. A differential refractive index detector (manufactured by Shimadzu Corp., trade name: RID-10A) was used as a detector.

<Example 1> Synthesis of Compound A-1

Compound A-1 represented by the formula (A-1) was synthesized by the following method.

[Chemical Formula 16]

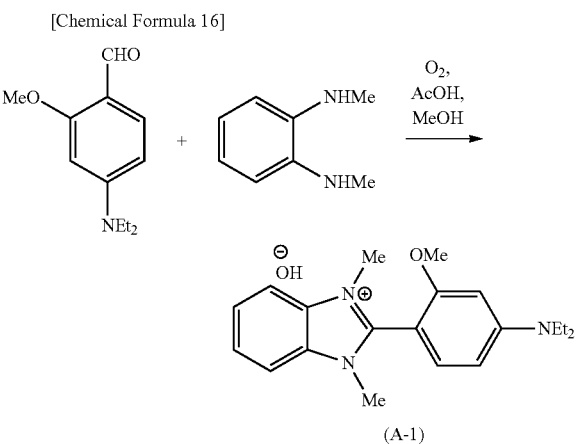

(A-1)

694 mg of N,N'-dimethyl-o-phenylenediamine and 1.28 g of 2-methoxy-4-diethylamino-benzaldehyde were dissolved in 10 ml of methanol, and a catalytic amount of acetic acid was added thereto. After being refluxed for 13 hours in an air atmosphere, the reaction product was concentrated. 10 ml of water was added thereto, and the mixture was washed three times with 10 ml of toluene. The aqueous phase was concentrated and dried overnight in a vacuum dryer of 50° C. 10 ml of an aqueous solution containing 5% by weight of sodium carbonate was added thereto, and the mixture was washed three times with 10 ml of toluene and then washed three times with 10 ml of chloroform. The aqueous phase was extracted with 100 ml of chloroform five times, the extract was dried over magnesium sulfate and then filtered, the organic phase was concentrated, and dried in a vacuum oven at 50° C., 795 mg of compound A-1 was obtained.

Analysis results about the obtained compound A-1 were as follows.
*$^1$H-NMR (CDCl$_3$)
δ 1.27 (6H, t), 3.48 (4H, q), 3.87 (3H, s), 3.97 (6H, s), 6.25 (1H, s), 6.50-6.52 (1H, m), 7.46 (1H, m), 7.64-7.66 (2H, m), 7.84-7.86 (2H, m)
*TLC-MS (DART)
310.14 ([M-CH$_2$]$^+$, Exact Mass: 324.21)

<Example 2> Synthesis of Compound A-2

Compound A-2 represented by the formula (A-2) was synthesized by the following method.

[Chemical Formula 17]

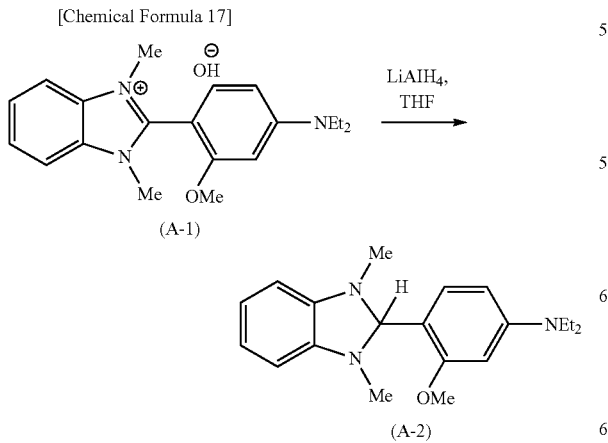

500 mg of compound A-1 was taken into a flask, and the atmosphere in the flask was purged with nitrogen. The compound was dissolved in 10 ml of dehydrated THF, and 107 mg of lithium aluminum hydride was added thereto in small portions and reacted at room temperature for 3 hours. 70 ml of water was taken into another flask and ice-cooled, and the reaction product was added dropwise thereto using a cannula. Extraction was performed with 20 ml of toluene four times, and the extract was dehydrated over sodium sulfate. The resultant was filtered, the organic phase was concentrated, and dried in a vacuum oven, 356 mg of compound A-2 was obtained.

Analysis results about the obtained compound A-2 were as follows.
*$^1$H-NMR (400 MHz, CDCl$_3$)
δ 1.19 (6H, t), 2.56 (6H, s), 3.37 (4H, q), 3.81 (3H, s), 5.45 (1H, s), 6.18 (1H, s), 634-6.37 (3H, m), 6.64-6.67 (21-1, m), 7.56 (1H, d)
*TLC-MS (DART)
326.17 ([M+]$^+$, Exact Mass: 325.22)

<Example 3> Synthesis of Compound A-3

Compound A-3 represented by the formula (A-3) was synthesized by the following methods of (i) to (iii).

[Chemical Formula 18]

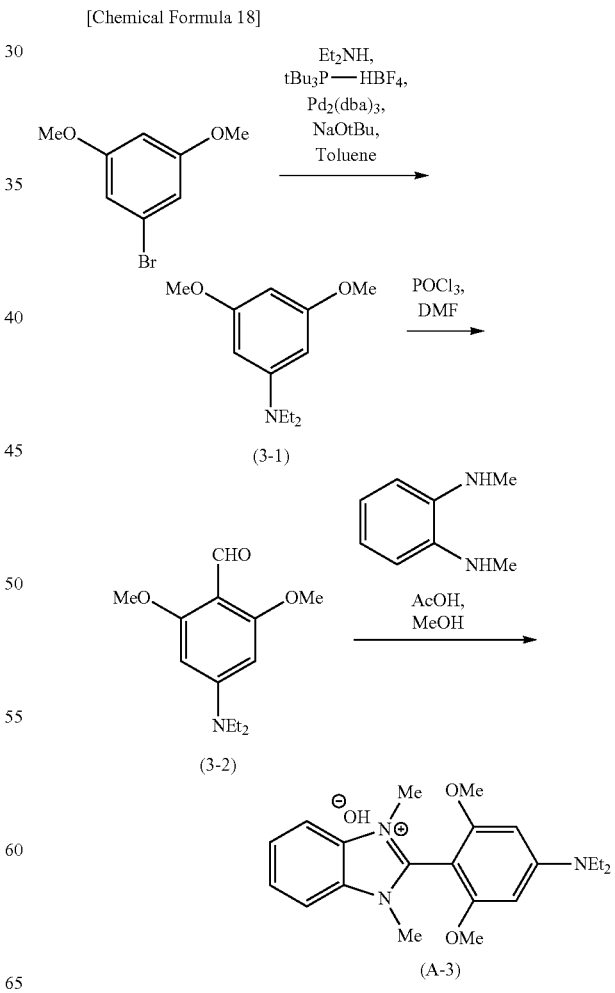

(i) Synthesis of Compound (3-1)

20.14 g of 3,5-dimethoxy-1-bromobenzene, 1.68 g of Pd$_2$(dba)$_3$, 2.38 g of tBu$_3$P—HBF$_4$, and 13.28 g of NaOtBu were taken into a flask, and the atmosphere in the flask was purged with nitrogen. 200 ml of toluene (dehydrated) was added thereto and heated to 80° C. in an oil bath. 14.4 ml of diethylamine was added dropwise thereto, incubated for 2 hours, and stirred. The resultant was cooled to 0° C., and 100 ml of water was added dropwise thereto for solution separation and extracted with 100 ml of toluene twice. The organic phases were combined and dried over magnesium sulfate, and as a result of distilling off the solvent, 24.07 g of a crude product was obtained. 15.98 g of compound (3-1) was obtained by purification (mobile phase, hexane:ethyl acetate) using silica gel column chromatography.

Analysis results about the obtained compound (3-1) were as follows.

*$^1$H-NMR (CDCl$_3$)

δ1.15 (6H, t), 3.31 (4H, q), 3.77 (6H, s), 5.84-5.87 (3H, m)

*TLC-MS (DART)

210.12 ([M+H]$^+$, Exact Mass: 209.14)

(ii) Synthesis of Compound (3-2)

The atmosphere in a flask was purged with nitrogen, and 18 ml of dehydrated DMF was added thereto. 4.8 ml of phosphorus oxychloride was added dropwise thereto while the internal temperature was kept at 10° C. or lower by cooling in an ice bath. After incubation for 30 minutes, a solution of 10.00 g of compound (3-1) dissolved in 6.0 ml of DMF was added dropwise thereto while the internal temperature was kept at 10° C. or lower. After stirring for 2.5 hours, the reaction product was added dropwise to a beaker supplemented with 42 g of ice water, and stirred for 2 hours. The aqueous phase was extracted with 125 ml of chloroform three times, and the organic phases were combined and washed with 100 ml of water and 100 ml of saturated saline. After drying over magnesium sulfate, the solvent was distilled off to obtain 27.85 g of a crude product. 12.13 g of compound (3-2) was obtained by purification (mobile phase, hexane:ethyl acetate) using silica gel column chromatography.

Analysis results about the obtained compound (3-2) were as follows.

*$^1$H NMR (CDCl$_3$)

δ 1.24 (6H, t), 3.42 (4H, q), 3.87 (6H, s), 5.73 (2H, s), 10.23 (1H, s)

*TLC-MS (DART)

238.14 ([M+H]$^+$, Exact Mass: 237.14)

(iii) Synthesis of Compound A-3

3.01 g of N,N'-dimethyl-o-phenylenediamine and 5.00 g of compound (3-2) were taken into a flask, and 42 ml of methanol was added thereto and stirred. 625 mg of acetic acid was added dropwise thereto and then heated at 70° C. for 14 hours in an air atmosphere. The reaction product was concentrated, supplemented with 10 ml of water, and washed three times with 50 ml of toluene. The aqueous phase was concentrated, then dissolved in 150 ml of chloroform, dried over magnesium sulfate, and filtered, then the solvent was distilled off, and dried in a vacuum oven, 6.16 g of compound A-3 was obtained.

Analysis results about the obtained compound A-3 were as follows.

*$^1$H-NMR (CDCl$_3$)

δ 1.29 (6H, t), 3.48 (4H, q), 3.83 (6H, s), 3.88 (6H, s), 5.91 (2H, s), 7.64-7.67 (2H, m), 7.88-7.92 (2H, m)

<Example 4> Synthesis of Compound A-4

Compound A-4 represented by the formula (A-4) was synthesized by the following method.

[Chemical Formula 19]

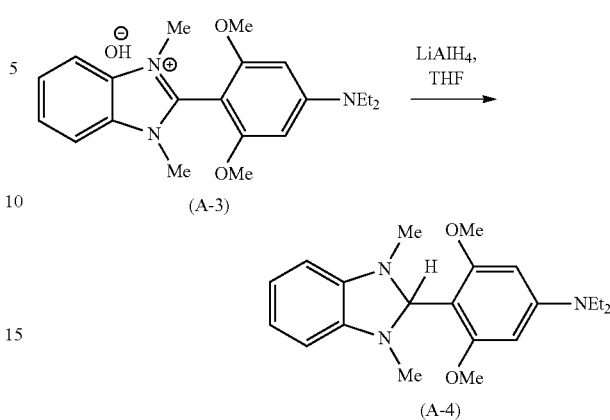

5.45 g of compound A-3 was taken into a flask, the atmosphere within the flask was purged with nitrogen, and then 109 ml of dehydrated THF was added thereto. 571 mg of lithium aluminum hydride was added thereto in small portions while the internal temperature was kept at 30° C. or lower in a water bath, and stirred for 3 hours. 750 g of ice water was taken, and the reaction solution was added dropwise thereto. Extraction was performed with 750 ml of toluene three times, the organic phases were combined, dried over sodium sulfate, and then filtered, and as a result of distilling off the solvent, 2.91 g of compound A-4 was obtained.

Analysis results about the obtained compound A-4 were as follows.

*$^1$H-NMR (CDCl$_3$)

δ 1.20 (6H, t), 2.55 (6H, s), 3.36 (4H, q), 3.67 (6H, brs), 5.86 (2H, s), 6.07 (1H, s), 6.20-6.23 (2H, m), 6.53-6.56 (2H, m)

*TLC-MS (DART)

355.24 ([M]$^+$, Exact Mass: 355.23)

<Example 5> Synthesis of Compound A-5

Compound A-5 represented by the formula (A-5) was synthesized by the following methods of (i) and (ii).

[Chemical Formula 20]

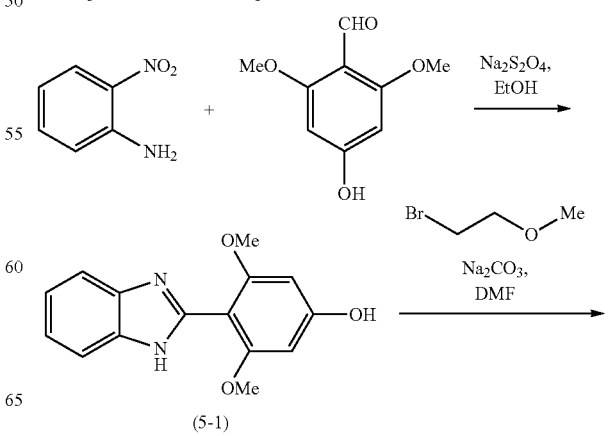

-continued

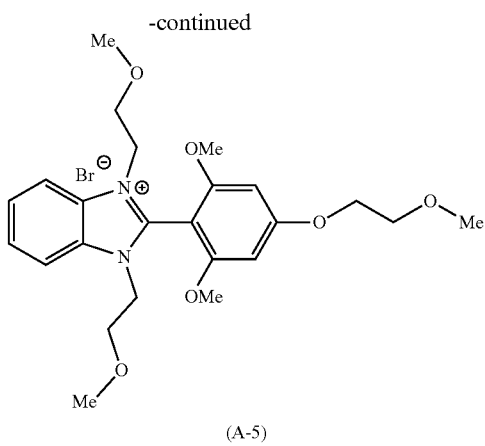

(A-5)

(i) Synthesis of Compound (5-1)

1.00 g of 2,6-dimethyl-4-hydroxybenzaldehyde and 0.76 g of 2-nitroaniline were taken, and the atmosphere in the flask was purged with nitrogen. A suspension was prepared by adding 27 ml of dehydrated ethanol, and then, 8 ml of a 1 M aqueous $Na_2S_2O_4$ solution was added dropwise thereto. The mixture was stirred at room temperature for 1 hour, then stirred at a bath temperature of 50° C. for 2 hours and at 80° C. for 5 hours, then further supplemented with 8 ml of a 1 M aqueous $Na_2S_2O_4$ solution, and further stirred for 2 hours. After standing to cool to room temperature, the resultant was filtered through a Kiriyama funnel and washed with 20 ml of ethanol. The obtained solid was dried, and then, 973 mg of a crude product was obtained. 12 ml of 5 N ammonia water was added to the filtrate and the washes, and the mixture was filtered through a Kiriyama funnel and washed with 15 ml of ethanol. The obtained solid was dried, and then, 1.650 g of a solid was obtained. Because of containing an inorganic salt, 8 ml of water was added thereto, and the mixture was stirred for 1 hour, then filtered, and washed three times with 2 ml of water. After drying, 384 mg of compound. (5-1) was obtained.

Analysis results about the obtained compound (5-1) were as follows.

*$^1$H-NMR (Dimethyl Sulfoxide-$d_6$)

δ 3.63 (6H, s), 6.18 (2H, s), 7.11-7.14 (2H, m), 7.48 (2H, brs)

*TLC-MS (DART)

271.12 ([M+H]$^+$, Exact Mass: 270.10)

(ii) Synthesis of Compound A-5

360 mg of compound (5-1) and 753 mg of 2-bromoethyl methyl ether were taken, and the atmosphere in the flask was purged with nitrogen. 2.0 ml of dehydrated. DMF was added thereto for suspension, and 571 mg of sodium carbonate was added thereto and reacted at a bath temperature of 110° C. for 6.5 hours. 5 ml of chloroform was added thereto, and the mixture was filtered through a Kiriyama funnel and washed twice with 2 ml of chloroform. The filtrate and the washes were concentrated to obtain 887 mg of a crude product. 572 mg of compound A-5 was obtained by purification using silica gel column chromatography (mobile phase, chloroform:methanol).

Analysis results about the obtained compound A-5 were as follows.

*$^1$H-NMR ($CDCl_3$)

δ 3.17 (6H, s), 3.49 (3H, s), 3.66 (4H, t), 3.82-3.86 (8H, m), 4.36-4.38 (2H, m), 4.49 (4H, t), 6.43 (2H, s), 7.64-7.67 (2H, m), 8.06-8.09 (2H, m)

*LC-MS (ESI-positive)

445.2 ([M]$^+$, Exact Mass: 445.23)

<Example 6> Synthesis of Compound A-6

Compound A-6 represented by the formula (A-6) was synthesized by the following method.

[Chemical Formula 21]

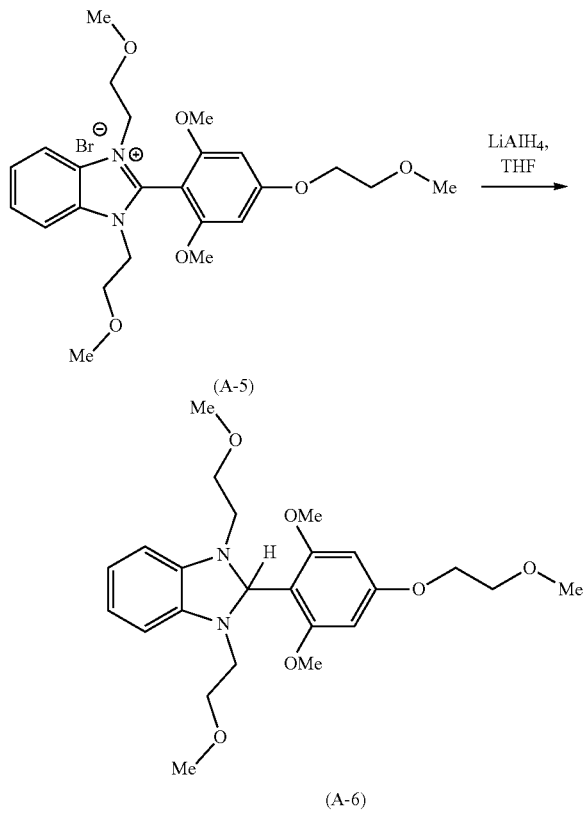

280 mg of compound A-5 was taken, the atmosphere in the flask was purged with nitrogen, and then, a suspension was prepared by adding 5.6 ml of dehydrated THF. 39.7 mg of lithium aluminum hydride was added thereto and stirred at room temperature for 7 hours, and then, 12.0 mg of lithium aluminum hydride was further added thereto and stirred for 6.5 hours. 40 ml of water was taken into a 300 ml beaker and cooled in an ice bath. The reaction product was added dropwise thereto. Extraction was performed with 20 ml of toluene three times, and the extract was dried over sodium sulfate. The resultant was filtered, washed with toluene, the solvent was distilled off, and then, dried in a vacuum oven to obtain 130 mg of compound A-6.

Analysis results about the obtained compound A-6 were as follows.

*$^1$H-NMR ($CDCl_3$)

δ 2.95-3.04 (2H, in), 3.13-3.22 (2H, m), 3.26 (6H, s), 331-3.38 (4H, m), 3.46 (3H, s), 3.60-3.90 (6H, brs), 3.73-3.77 (2H, m), 4.10-4.13 (2H, m), 6.14 (2H, s), 6.16-6.19 (2H, m), 6.47-6.51 (2H, m), 6.66 (1H, s)

*TLC-MS (DART)

447.27 ([M+H]$^+$, Exact Mass: 446.24)

Synthesis Example 1: Synthesis of Polymer Compound P-1

Polymer compound P-1 having a repeat unit represented by the formula (P-1) was synthesized by (Step 1) to (Step 4) given below. Compound (M-1) represented by the formula (M-1) and compound (M-2) represented by the formula (M-2) were used as monomers of raw materials.

[Chemical Formula 22]

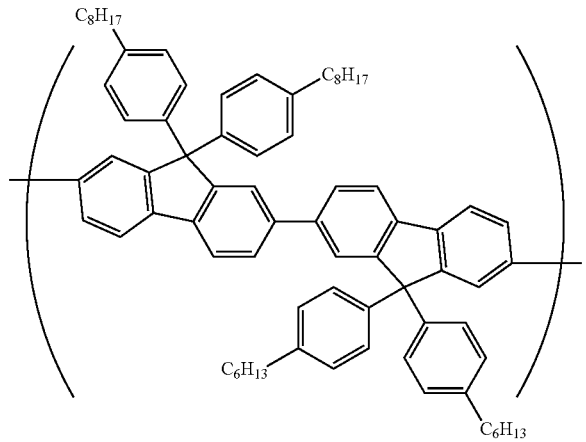

(P-1)

[Chemical Formula 23]

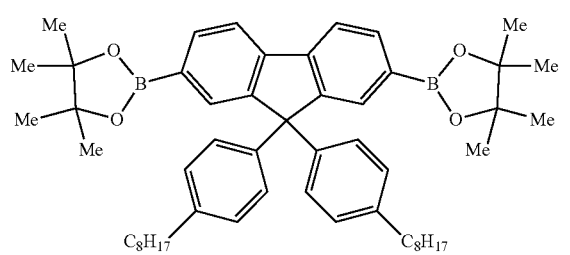

(M-1)

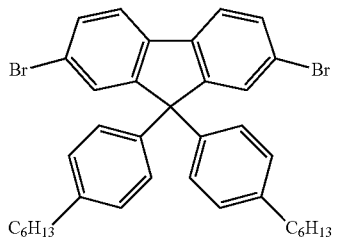

(M-2)

(Step 1) After an inert gas atmosphere was created in a reaction vessel, compound (M-1) (3.559 g), compound (M-2) (2.900 g), bis(triphenylphosphine)palladium(II) dichloride (3.2 mg) and toluene (50 mL) were added and heated to 105° C.
(Step 2) Then, an aqueous solution containing 20% by weight of tetraethylammonium hydroxide (15 mL) was added dropwise thereto and refluxed for 3 hours.
(Step 3) Then, phenylboronic acid (54.9 mg) and toluene (50 mL) were added thereto and refluxed for 12 hours or longer.
(Step 4) Then, an aqueous sodium diethyldithiocarbamate solution was added thereto and stirred at 80° C. for 2 hours. The obtained reaction mixture was cooled and then washed twice with water, twice with an aqueous solution containing 3% by weight of acetic acid and twice with water. The obtained solution was added dropwise to methanol, and as a result of stirring, precipitates were formed. The obtained precipitates were dissolved in toluene and purified by passing the solution through an alumina column and a silica gel column in order. The obtained solution was added dropwise to methanol, and as a result of stirring, precipitates were formed. The obtained precipitates were taken by filtration and dried to thereby obtain 3.93 g of polymer compound P-1.

The number-average molecular weight (Mn) of the obtained polymer compound P-1 was $1.9 \times 10^5$, and the weight-average molecular weight (Mw) was $5.1 \times 10^5$. The polymer compound P-1 is a copolymer in which a constitutional unit derived from compound (M-1) and a constitutional unit derived from compound (M-2) are constituted at a molar ratio of 50:50, in terms of a theoretical value determined from the amounts of the added raw materials.

The compound (M-1) was synthesized according to the method described in Japanese Unexamined Patent Publication No. 2014-224101. Also, the compound (M-2) was synthesized according to the method described in International Publication No. WO 2009/131255.

Device Preparation Example 1: Preparation and Evaluation of Electron Only Device D1

(i) Formation of Anode
An ITO film was attached at a thickness of 45 nm to a glass substrate by the sputtering method to thereby form an anode.

(ii) Formation of Thin Film
Polymer compound P-1 was used as an electron-transporting material, and a solution of 16 mg of the polymer compound P-1 and 4 mg of compound A-4 dissolved in xylene was provided. A film was formed on the substrate with the anode formed by the spin coating method using this solution so as to attain a thickness of 80 nm, and in a nitrogen gas atmosphere, a thin film was formed by heating at 50° C. for 10 minutes.

(iii) Formation of Cathode
The substrate with the thin film formed was placed in a vapor deposition machine, and after pressure reduction to $1.0 \times 10^{-4}$ Pa or lower, silver (work function: 4.5 eV) as a cathode was deposited at 150 nm on the thin film. After the deposition, the resultant was sealed using a glass substrate.

(iv) Activation
After the formation of the cathode, electron only device D1 was prepared by irradiation with a light of 365 nm for 1 hour.

(v) Evaluation
A current density was measured by applying voltage of 6 V to the electron only device D1. The current density at the time of application of voltage of 6 V was 532 mA/cm².

Device Preparation Example 2: Preparation and Evaluation of Electron Only Device D2

Electron only device D2 was prepared in the same way as in Device Preparation Example 1 except that compound A-2 was used instead of the compound A-4. The obtained electron only device D2 had a current density of 121 mA/cm² at the time of application of 6 V.

Device Preparation Comparative Example 1: Preparation and Evaluation of Electron Only Device CD1

Electron only device CD1 was prepared in the same way as in Device Preparation Example 1 except that the compound A-4 was not added. The obtained electron only device CD1 had a current density of $2 \times 10^{-6}$ mA/cm$^2$ at the time of application of 6 V.

<Device Preparation Comparative Example 2>
Preparation and Evaluation of Electron Only Device CD2

Electron only device CD2 was prepared in the same way as in Device Preparation Example 1 except that N-DMBI represented by the following formula was used instead of the compound A-4. The obtained electron only device CD2 had a current density of 0.6 mA/cm$^2$ at the time of application of 6 V. N-DMBI was purchased from Sigma-Aldrich Co. LLC.

[Chemical Formula 24]

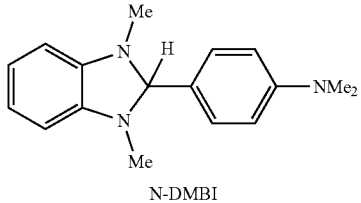

N-DMBI

<Device Preparation Comparative Example 3>
Preparation and Evaluation of Electron Only Device CD3

Electron only device CD3 was prepared in the same way as in Device Preparation Example 1 except that a compound represented by the formula (a-1) was used instead of the compound A-4. The obtained electron only device CD3 had a current density of $2 \times 10^{-4}$ mA/cm$^2$ at the time of application of 6 V. The compound represented by the formula (a-1) was purchased from Sigma-Aldrich Co. LLC.

[Chemical Formula 25]

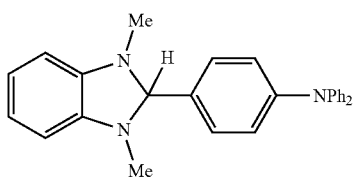

(a-1)

INDUSTRIAL APPLICABILITY

The compound according to the present invention is relatively stable in a solvent, can be applied to film formation by a coating method, and suitably functions as an n-type doping material. Also, the compound according to the present invention can dope an electron-transporting material more strongly by mixing with the electron-transporting material, as compared with a publicly known n-type doping material that permits film formation by a coating method.

The invention claimed is:

1. A compound represented by the formula (1):

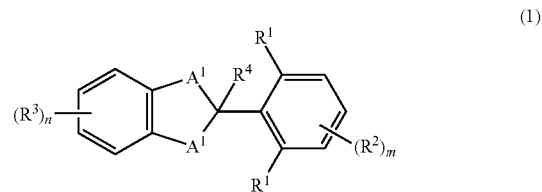

(1)

wherein
$A^1$ represents —NR$^5$— or —PR$^5$—, two $A^1$ are the same as or different from each other;
$R^1$ represents a hydrogen atom, an alkyl group, a cycloalkyl group, an alkoxy group, a cycloalkoxy group, an aryloxy group, an alkylsulfenyl group, a cycloalkylsulfenyl group, an arylsulfenyl group or a disubstituted amino group; —CH$_2$— in these groups is optionally replaced with an oxygen atom, a sulfur atom, —NR$^5$— or —C(=O)O—, and a portion or the whole of hydrogen atoms in these groups is optionally substituted with a halogen atom, provided that adjacent two —CH$_2$— are not replaced at the same time; two $R^1$ are the same as or different from each other;
$R^2$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —CH$_2$— in these groups is optionally replaced with an oxygen atom, a sulfur atom, —NR$^5$— or —C(=O)O—, and a portion or the whole of hydrogen atoms in these groups is optionally substituted with a halogen atom, provided that adjacent two —CH$_2$— are not replaced at the same time; in the case where m is 2 or larger, the plurality of $R^2$ are the same as or different from each other; or adjacent $R^2$ are optionally bonded to each other to form a ring;
$R^3$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —CH$_2$— in these groups is optionally replaced with an oxygen atom, a sulfur atom, —NR$^5$— or —C(=O)O—, and a portion or the whole of hydrogen atoms in these groups is optionally substituted with a halogen atom, provided that adjacent two —CH$_2$— are not replaced at the same time; in the case where n is 2 or larger, the plurality of $R^3$ are the same as or different from each other; or adjacent $R^3$ are optionally bonded to each other to form a ring,
provided that
in the case where n is 0 or in the case where $R^3$ is not a disubstituted amino group, at least one $R^1$ is an alkoxy group, a cycloalkoxy group, an aryloxy group, an alkylsulfenyl group, a cycloalkylsulfenyl group, an arylsulfenyl group or a disubstituted amino group, and
in the case where any of $R^1$, $R^2$ and $R^3$ are not a disubstituted amino group, both $R^1$ are groups other than a hydrogen atom, and at least one $R^1$ is an alkoxy group, a cycloalkoxy group, an aryloxy group, an alkylsulfenyl group, a cycloalkylsulfenyl group or an arylsulfenyl group;

$R^4$ represents a hydrogen atom, $-C(R^6)_3$, $-N(R^7)_2$ or $-Si(R^7)_3$; $-CH_2-$ in these groups is optionally replaced with an oxygen atom, a sulfur atom, $-NR^5-$ or $-C(=O)O-$, and a portion or the whole of hydrogen atoms in these groups is optionally substituted with a halogen atom, provided that adjacent two $-CH_2-$ are not replaced at the same time;

$R^5$ represents an alkyl group, a cycloalkyl group, an aryl group or a monovalent heterocyclic group; $-CH_2-$ in these groups is optionally replaced with an oxygen atom, a sulfur atom, $-NR^8-$ or $-C(=O)O-$, and a portion or the whole of hydrogen atoms in these groups is optionally substituted with a halogen atom, provided that adjacent two $-CH_2-$ are not replaced at the same time; when a plurality of $R^5$ are present, the plurality of $R^5$ are the same as or different from each other;

$R^6$ represents a hydrogen atom, an alkyl group, a cycloalkyl group, an aryl group or a monovalent heterocyclic group; a portion or the whole of hydrogen atoms in these groups is optionally substituted with a halogen atom; the plurality of $R^6$ are the same as or different from each other; or two $R^6$ are optionally bonded to form a ring;

$R^7$ represents an alkyl group, a cycloalkyl group, an aryl group or a monovalent heterocyclic group; a portion or the whole of hydrogen atoms in these groups is optionally substituted with a halogen atom; a plurality of $R^7$ are the same as or different from each other; or two $R^7$ are optionally bonded to form a ring;

$R^8$ represents an alkyl group, a cycloalkyl group, an aryl group or a monovalent heterocyclic group; a portion or the whole of hydrogen atoms in these groups is optionally substituted with a halogen atom; when a plurality of $R^8$ are present, the plurality of $R^8$ are the same as or different from each other;

m represents an integer of 1 to 3; and n represents an integer of 0 to 4.

2. The compound according to claim 1, wherein both $A^1$ are $-NR^5-$.

3. The compound according to claim 1, wherein the compound is a compound represented by the formula (2):

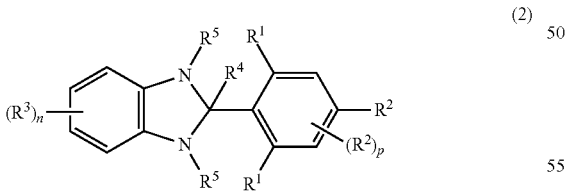

wherein $R^1$, $R^2$, $R^3$, $R^4$, $R^5$ and n are as defined in claim 1, and p represents an integer of 0 to 2.

4. The compound according to claim 1, wherein $R^4$ is a hydrogen atom.

5. A composition comprising the compound according to claim 1 and an electron-transporting material.

6. The composition according to claim 5, further comprising a solvent.

7. A method for producing the compound according to claim 1, comprising a step of reacting a compound represented by the formula (3) with a compound represented by the formula (4):

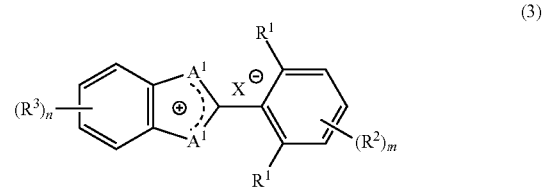

wherein $A^1$, $R^1$, $R^2$, $R^3$, m and n are as defined in claim 1, and $X^-$ represents a counter anion for the cation, and $$M^1{}_q(M^2\text{-}R^4{}_r)_s \qquad (4)$$

wherein $R^4$ is as defined in claim 1, $M^1$ and $M^2$ each independently represent a group containing a metal atom or a metalloid atom, q represents an integer of 0 to 3, r represents an integer of 1 to 4, and s represents an integer of 1 to 3.

8. The method according to claim 7, wherein $R^4$ is a hydrogen atom, and $M^2$ is an aluminum atom.

9. A compound represented by the formula (1):

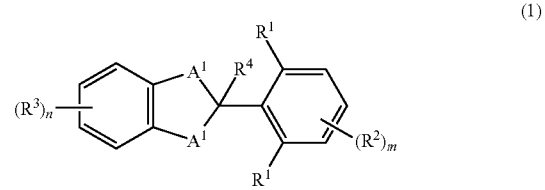

wherein $A^1$ represents $-NR^5-$ or $-PR^5-$; two $A^1$ are the same as or different from each other;

$R^1$ represents a hydrogen atom, an alkyl group, a cycloalkyl group, an alkoxy group, a cycloalkoxy group, an aryloxy group, an alkylsulfenyl group, a cycloalkylsulfenyl group or an arylsulfenyl group; $-CH_2-$ in these groups is optionally replaced with an oxygen atom, a sulfur atom, $-NR^5-$ or $-C(=O)O-$, and a portion or the whole of hydrogen atoms in these groups is optionally substituted with a halogen atom, provided that adjacent two $-CH_2-$ are not replaced at the same time; two $R^1$ are the same as or different from each other;

$R^2$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; $-CH_2-$ in these groups is optionally replaced with an oxygen atom, a sulfur atom, $-NR^5-$ or $-C(=O)O-$, and a portion or the whole of hydrogen atoms in these groups is optionally substituted with a halogen atom, provided that adjacent two $-CH_2-$ are not replaced at the same time; in the case where m is 2 or larger, the plurality of $R^2$ are the same as or different from each other; or adjacent $R^2$ are optionally bonded to each other to form a ring;

$R^3$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time; in the case where n is 2 or larger, the plurality of $R^3$ are the same as or different from each other; or adjacent $R^3$ are optionally bonded to each other to form a ring, provided that in the case where n is 0 or in the case where $R^3$ is not a disubstituted amino group, at least one $R^1$ is an alkoxy group, a cycloalkoxy group, an aryloxy group, an alkylsulfenyl group, a cycloalkylsulfenyl group or an arylsulfenyl group, and in the case where any of $R^2$ and $R^3$ are not a disubstituted amino group, both $R^1$ are groups other than a hydrogen atom, and at least one $R^1$ is an alkoxy group, a cycloalkoxy group, an aryloxy group, an alkylsulfenyl group, a cycloalkylsulfenyl group or an arylsulfenyl group;

$R^4$ represents a hydrogen atom, —$C(R^6)_3$, —$OR^7$, —$N(R^7)_2$ or —$Si(R^7)_3$; —$CH_2$— in these groups is optionally replaced with an oxygen atom, a sulfur atom, —$NR^5$— or —C(=O)O—, and a portion or the whole of hydrogen atoms in these groups is optionally substituted with a halogen atom, provided that adjacent two —$CH_2$— are not replaced at the same time;

$R^5$ represents an alkyl group, a cycloalkyl group, an aryl group or a monovalent heterocyclic group; —$CH_2$— in these groups is optionally replaced with an oxygen atom, a sulfur atom, —$NR^8$— or —C(=O)O—, and a portion or the whole of hydrogen atoms in these groups is optionally substituted with a halogen atom, provided that adjacent two —$CH_2$— are not replaced at the same time; when a plurality of $R^5$ are present, the plurality of $R^5$ are the same as or different from each other;

$R^6$ represents a hydrogen atom, an alkyl group, a cycloalkyl group, an aryl group or a monovalent heterocyclic group; a portion or the whole of hydrogen atoms in these groups is optionally substituted with a halogen atom; the plurality of $R^6$ are the same as or different from each other; or two $R^6$ are optionally bonded to form a ring;

$R^7$ represents an alkyl group, a cycloalkyl group, an aryl group or a monovalent heterocyclic group; a portion or the whole of hydrogen atoms in these groups is optionally substituted with a halogen atom; a plurality of $R^7$ are the same as or different from each other; or two $R^7$ are optionally bonded to form a ring;

$R^8$ represents an alkyl group, a cycloalkyl group, an aryl group or a monovalent heterocyclic group; a portion or the whole of hydrogen atoms in these groups is optionally substituted with a halogen atom; when a plurality of $R^8$ are present, the plurality of $R^8$ are the same as or different from each other;

m represents an integer of 0 to 3; and n represents an integer of 0 to 4.

* * * * *